United States Patent [19]
Shuler et al.

[11] Patent Number: 5,957,946
[45] Date of Patent: Sep. 28, 1999

[54] SURGICAL BONE AWL

[75] Inventors: Thomas E. Shuler, Roanoke, Va.; Robert A. Latour, Jr., Clemson, S.C.

[73] Assignee: Lab Medical Engineering & Manufacturing, North Billerica, Mass.

[21] Appl. No.: 09/050,714

[22] Filed: Mar. 30, 1998

Related U.S. Application Data

[60] Provisional application No. 60/051,744, Jul. 30, 1997.

[51] Int. Cl.⁶ .................................................. A61B 17/16
[52] U.S. Cl. .............................. 606/184; 606/79; 606/84; 30/366
[58] Field of Search .................................. 606/79, 80, 84, 606/85, 184, 185; 30/358, 366, 164.5, 164.7, 164.9, 340, 342, 337, 329; 81/177.85

[56] References Cited

U.S. PATENT DOCUMENTS

| | | | |
|---|---|---|---|
| 3,036,482 | 5/1962 | Kenworthy et al. | 173/90 |
| 3,803,667 | 4/1974 | Rose | 606/1 |
| 4,509,223 | 4/1985 | Sipple et al. | 15/160 |
| 4,867,158 | 9/1989 | Sugg . | |
| 5,351,404 | 10/1994 | Smith . | |
| 5,368,595 | 11/1994 | Lewis . | |
| 5,368,596 | 11/1994 | Burkhart . | |
| 5,382,257 | 1/1995 | Lewis et al. . | |
| 5,490,852 | 2/1996 | Azer et al. . | |
| 5,562,673 | 10/1996 | Koblish et al. . | |

*Primary Examiner*—Michael Buiz
*Assistant Examiner*—David O. Reip
*Attorney, Agent, or Firm*—Dority & Manning, P.A.

[57] ABSTRACT

A surgical awl is provided for orthopaedic applications that include creating or enlarging holes in bone. The awl has a shaft and a cutting tip that has a working end and an opposite attachment end, which mechanically locks in place into a recess formed in the end of the shaft opposite the handle. A release mechanism is provided to allow the user to selectively disengage the cutting tip from the shaft. The awl has a hole-retention sleeve which surrounds at least part of the awl shaft and the awl tip and could be configured to surround the entire shaft and tip. The retention sleeve has a forward cutting edge. A protective sleeve may be used in place of the retention sleeve to protect the manual awl tip release mechanism from being accidentally activated to release the awl tip.

10 Claims, 9 Drawing Sheets

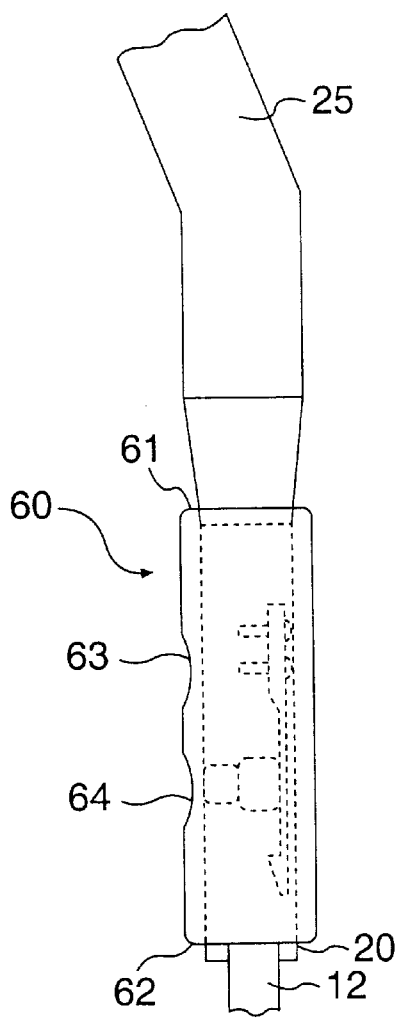
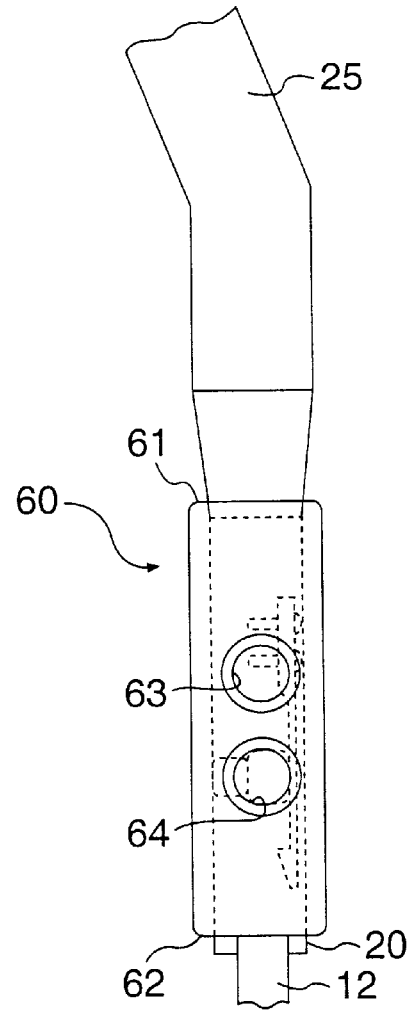
FIG. 7B  FIG. 7C

SURGICAL BONE AWL

PRIORITY CLAIM

The present application hereby claims priority based on provisional application Ser. No. 60/051,744, filed on Jul. 30, 1997.

BACKGROUND OF THE INVENTION

The present invention relates generally to a surgical bone awl.

Surgical awls are known and include the handheld variety such as shown in U.S. Pat. No. 5,490,852 to Azer; U.S. Pat. No. 5,562,673 to Koblish et al.; U.S. Pat. No. 5,368,595 to Lewis; U.S. Pat. No. 5,368,596 to Burkhart; and U.S. Pat. No. 5,382,257 to Lewis et al., as well as self-powered bone awls such as disclosed in U.S. Pat. No. 4,867,158 to Sugg. Common problems associated with one or more of the prior awl constructions include wear or damage to the tip of the awl. Additionally, after the awl forms a hole in the bone, it can become difficult to relocate the hole when the awl is withdrawn from the wound site.

OBJECTS AND SUMMARY OF THE INVENTION

The present invention recognizes and addresses the foregoing disadvantages, and others, of prior art constructions and methods. Accordingly, it is an object of the present invention to provide an improved surgical bone awl.

It is a further object of the present invention to provide an improved surgical bone awl with a retractable retention sleeve that maintains the puncture site on the bone after withdrawal of the awl tip from the site.

It is another object of the present invention to provide an improved surgical bone awl with a retractable retention sleeve that has a forward cutting edge capable of physically seating into the bone around the awl tip so as to maintain its position around the entrance hole produced by the awl tip.

It also is an object of the present invention to provide an improved surgical bone awl with an exchangeable tip that is easily replaced during the course of surgery, if necessary.

It is still another object of the present invention provide an improved surgical bone awl with retractable retention sleeve and exchangeable tip.

It is yet a further object of the present invention provide an improved surgical bone awl with a retractable sleeve that shields the release mechanism for an exchangeable tip.

These and other objects are achieved by a surgical awl for orthopaedic applications that include creating or enlarging holes in bone. The awl includes a shaft, which has a handle for awl manipulation. The awl further includes a cutting tip that has a working end and an opposite attachment end, which mechanically locks in place into a recess formed in the end of the shaft opposite the handle. The awl tip can also be quickly and easily released manually by a release mechanism such as a spring-biased button or other mechanism. Thus, different cutting tips can be easily and quickly mounted and dismounted from the shaft to allow the use of various tip designs, and the replacement of tips when they become dull. This enables the awl to be used for a variety of surgical applications, which include fracture fixation (for example: intramedullary nails) and joint replacement.

The mechanical locking of each cutting tip is such that when engaged in the shaft, the tip can support torsional, bending, and axial loads in all directions.

In a presently preferred embodiment of the invention, the shaft of the awl has a hole-retention sleeve, which can act as an integral part of the awl. The retention sleeve surrounds at least part of the awl shaft and awl tip and could be configured to surround the entire shaft and tip. The retention sleeve has a forward cutting edge that is able to physically seat into the bone around the awl tip so as to maintain its position around the entrance hole produced by the awl tip. The awl tip and shaft can then be withdrawn back out of the retention sleeve while the sleeve is maintained in position against the bone so as to provide and maintain access to the hole made by the awl tip. Other instruments (for example: guide rods, drills, reamers, awls) can then be passed through the sleeve and into the hole previously occupied by the awl tip. This feature is particularly useful for treating obese patients or in other situations where there is much soft tissue around the entrance hole. Use of the hole-retention sleeve thus maintains access to the entrance hole so that the hole position is not lost when the awl tip and shaft is withdrawn after making the entrance hole.

The awl can also be used without the hole-retention sleeve. When used without the retention sleeve, a protective sleeve may be used in place of the retention sleeve. Like the retention sleeve, the protective sleeve also can be positioned around part or all of the awl shaft and tip. The protective sleeve may act to protect soft-tissue from being caught on features (such as a spring or button) that may be present on the tip or shaft of the awl. The protective sleeve may also be used to protect the manual awl tip release mechanism from being accidentally activated to release the awl tip during surgery or other times when release of the awl tip is not desired.

Other objects and aspects of the present invention are provided by various combinations and subcombinations of the disclosed elements, which are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings, in which:

FIG. 7B is a side plan view of a presently preferred embodiment of the invention fitted with a protection sleeve and with the dashed lines indicating portions that would otherwise be hidden in the view shown;

FIG. 7C is a front plan view of a presently preferred embodiment of the invention fitted with a protection sleeve as in FIG. 7B and with the dashed lines indicating portions that would otherwise be hidden in the view shown;

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary constructions. The same numerals are used throughout the specification and drawings to reference the same features or corresponding features that are common to different embodiments. Moreover, features that are part of one embodiment can be combined with features of another embodiment to yield a yet further embodiment.

Figure 1:
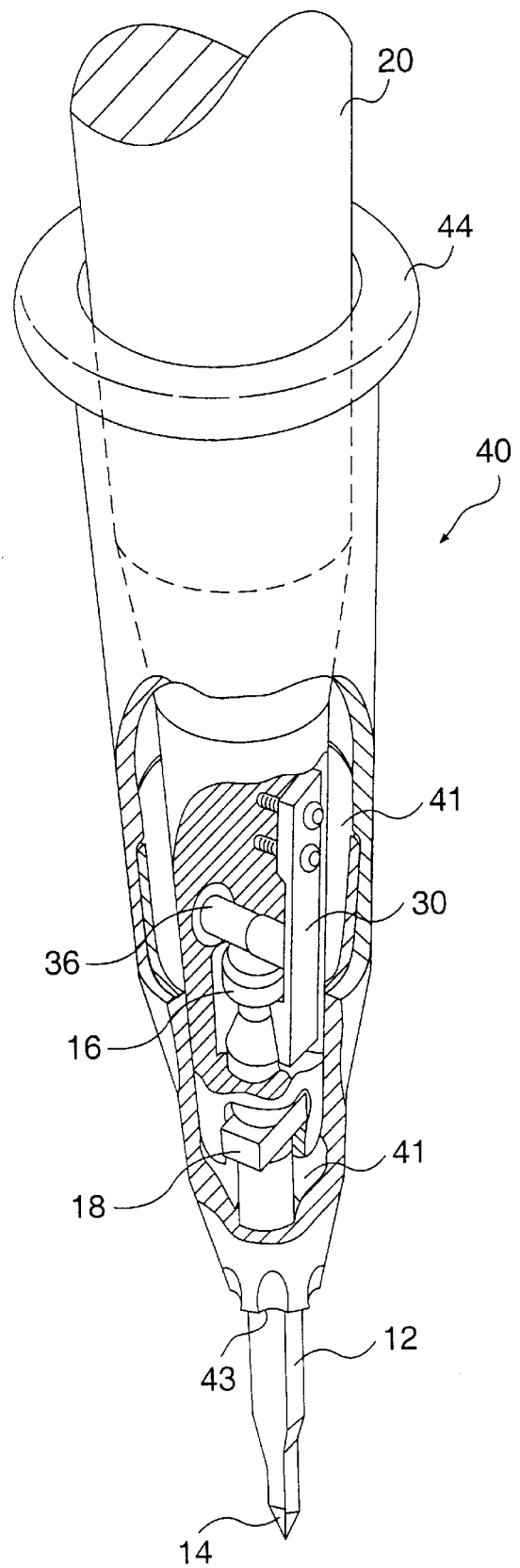
FIG. 1 is a partial, elevated perspective view of a presently preferred embodiment of the apparatus of the invention.
Figure 7A:
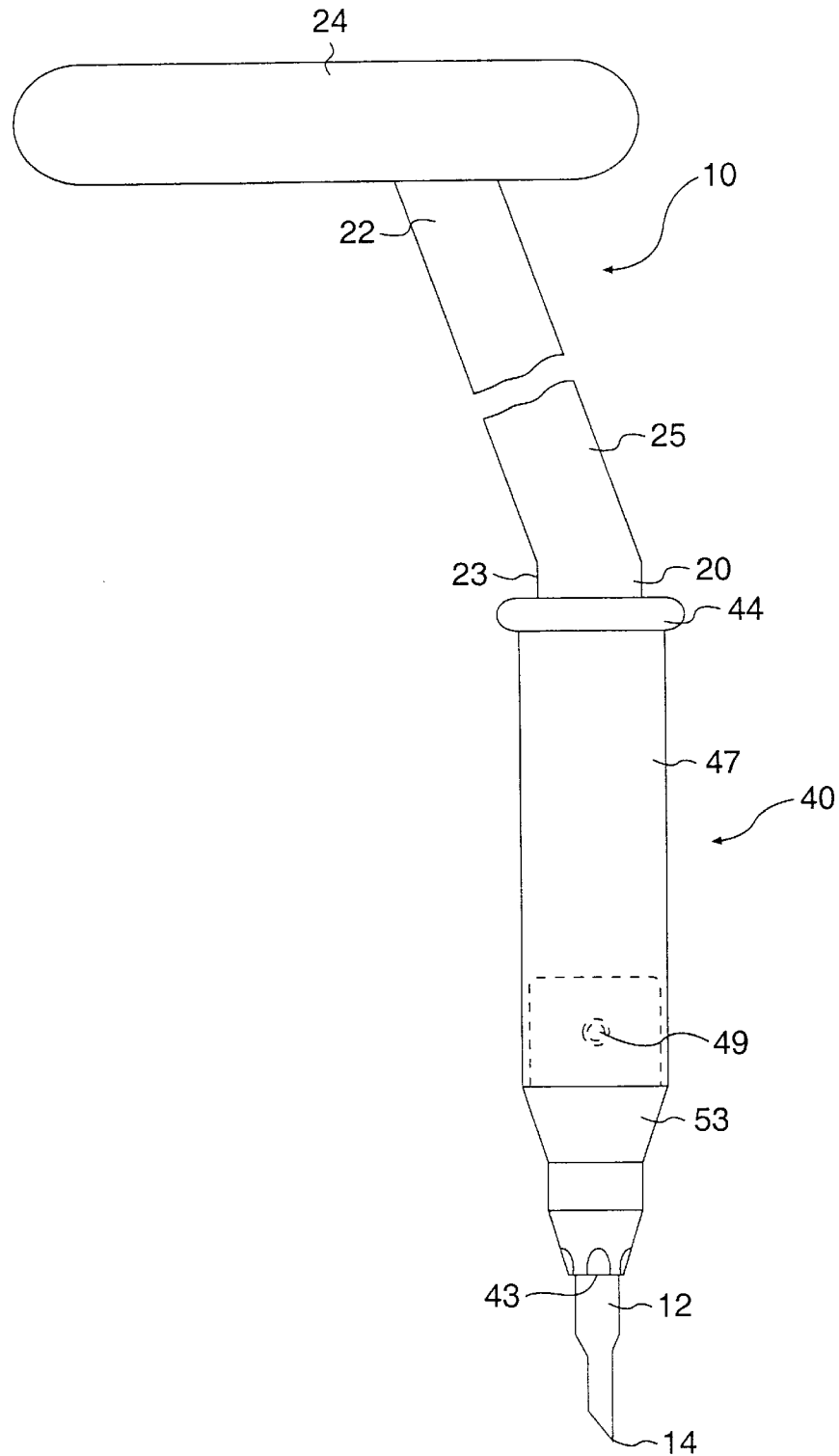
FIG. 7A is a side plan view of a presently preferred embodiment of the invention with the dashed lines indicating portions that would otherwise be hidden in the view shown.

In accordance with the present invention, a surgical bone awl is shown in FIG. 7A and designated generally by the numeral 10. FIG. 1 illustrates an enlarged view of portions of the awl 10 shown in FIG. 7A, with exterior sections cut away to expose to the viewer some of the operative components of the presently preferred embodiment.

Figure 4:
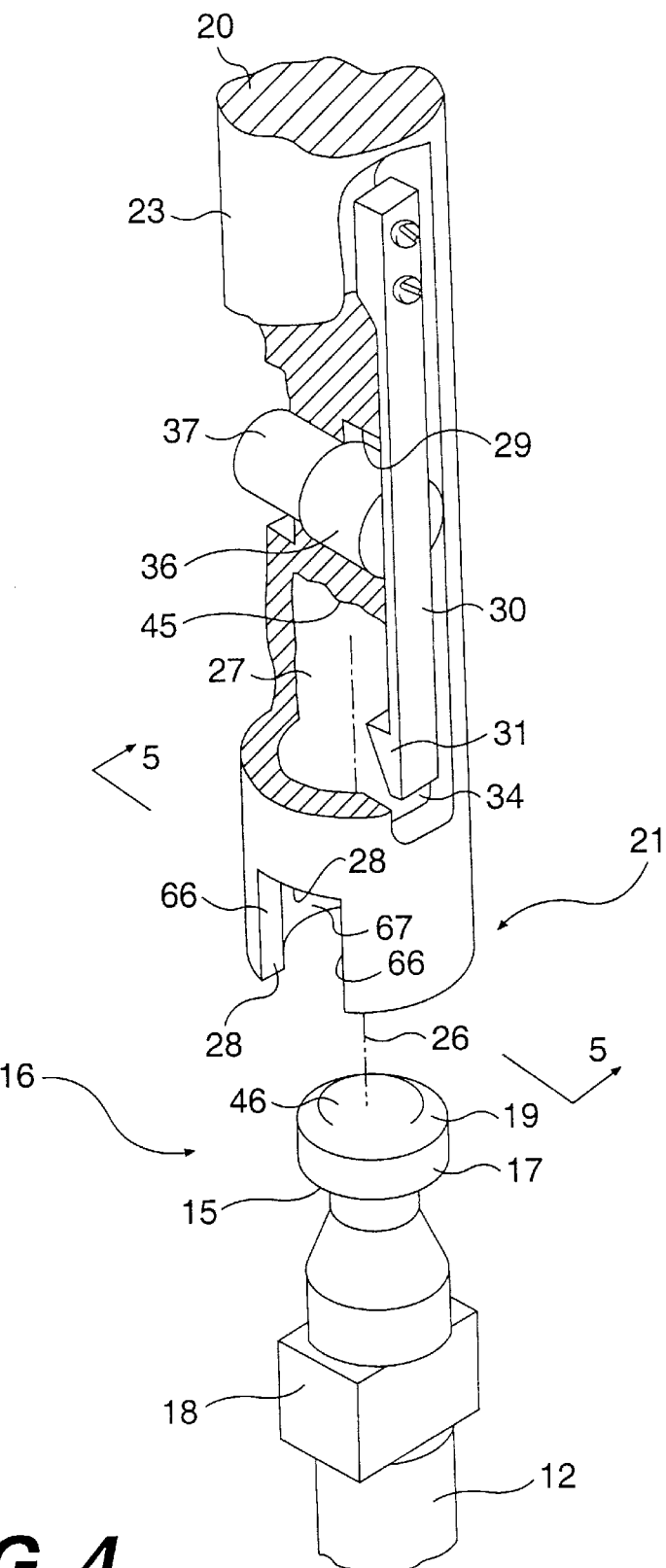
FIG. 4 is an assembly view from an elevated perspective view of a presently preferred embodiment of the locking mechanism component of the invention.

As shown in FIG. 1, an awl tip 12 defines a generally elongated rigid metal member having a working end 14 and an attachment end 16 disposed opposite working end 14. As shown in FIG. 4 for example, attachment end 16 of awl tip 12 defines a cam member 18 that is shaped like a cube. In addition, attachment end 16 of awl tip 12 further defines a radially extending lip 17 having a forward surface 46, which is at the free end of attachment end 16 in the embodiment shown in FIGS. 4 and 5. As shown in FIG. 4 for example, lip 17 also defines an underside surface 15 and a camferred surface 19.

In the views shown in FIGS. 1 and 7A for example, working end 14 of awl tip 12 is configured in the form of a tetrahedron. The present invention contemplates other configurations of working end 14 of awl tip 12. Thus, the working surface of any surgical instrument that lends itself to the configuration of the present invention, can be used to form working end 14 of awl tip 12. Moreover, it is contemplated that one of the advantages of the present invention is the ability to replace awl tips 12 when the working surfaces become worn or in disrepair. In addition, the present invention contemplates the ability to use different working surfaces on different awl tips 12, depending upon the desire of the surgeon.

As shown in FIGS. 1 and 7A, surgical bone awl 10 further defines a shaft 20. Shaft 20 has a receiving end designated generally in FIGS. 4 and 5 for example, by the numeral 21. Moreover, as shown in FIG. 7A, shaft 20 has a gripping end 22 disposed generally opposite receiving end 21.

As shown in FIG. 7A, a handle 24 is attached to gripping end 22 of shaft 20 and configured to facilitate the user's manipulation of awl 10. Handle 24 can be fabricated as a unitary structure with gripping end 22 of shaft 20. In addition, handle 24 can be fabricated as a separate structure from gripping end 22 and attached to gripping end 22 and thus rendered integral with shaft 20.

As shown in FIG. 7A, in a presently preferred embodiment, shaft 20 defines an axial portion 23 and an angled leg 25 that extends at an angle from the central axis 26 (FIG. 4) of axial portion 23 of shaft 20. Angled leg 25 provides a shaft configuration that facilitates the surgeon's manipulation of awl 10.

Figure 5:
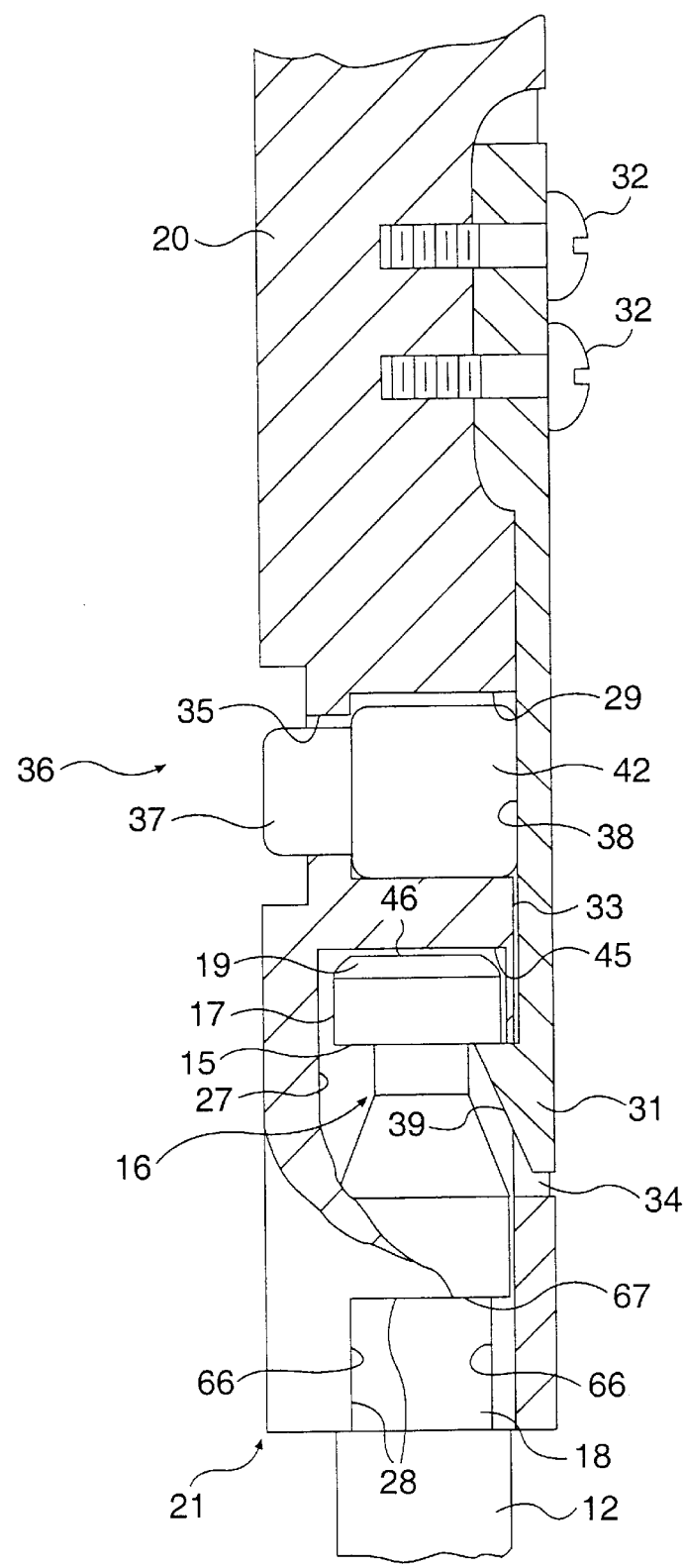
FIG. 5 is a cross-sectional view taken along a line of sight that looks in the direction of the arrows designated 5—5 in FIG. 4.
Figure 6:
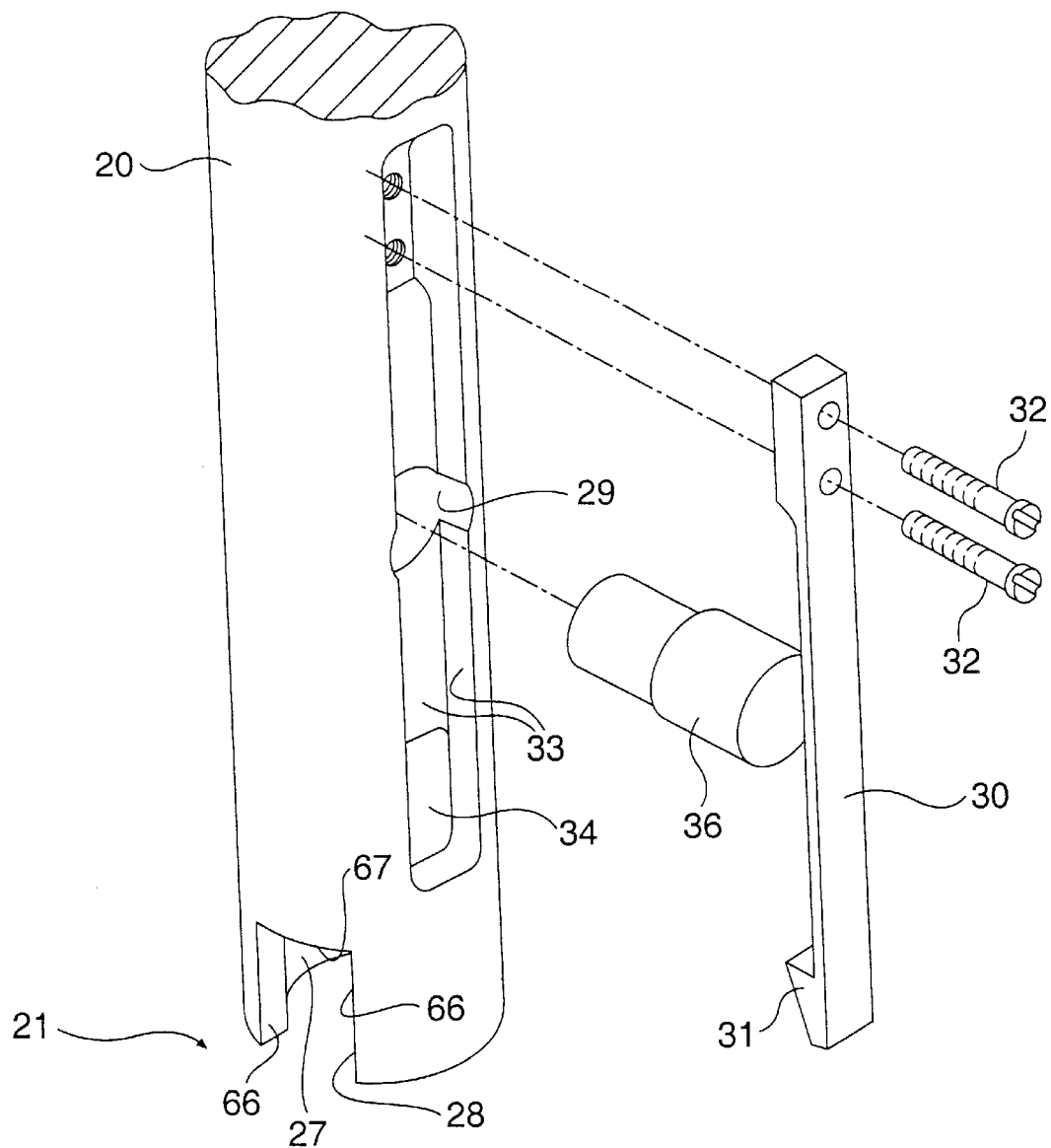
FIG. 6 is an elevated perspective view of a presently preferred embodiment of the release mechanism component of the invention.

As shown in FIGS. 4–6, shaft 20 defines a recess 27 in receiving end 21. Recess 27 is configured in the form necessary to receive attachment end 16 of awl tip 12 therein so that receiving end 21 is thereby configured to be selectively connected to attachment end 16 of awl tip 12. As shown in FIGS. 4 and 5, recess 27 defines a bottom 45 thereof. As shown in FIGS. 4–6, receiving end 21 of shaft 20 further defines a slot 28 configured with opposed, axially extending surfaces 66 that receive cam 18 so as to prevent rotation of awl tip 12 relative to shaft 20 when attachment end 16 of awl tip 12 is received in recess 27. Slot 28 thus functions as part of a locking mechanism to retain awl tip 12 against rotational movement relative to shaft 20 when attachment end 16 of awl tip 12 is received in recess 27. Accordingly, slot 28 and cam 18 cooperate so as to retain awl tip 12 fixed against rotational movement with respect to shaft 20 while undergoing twisting loads. In addition, slot 27 is configured with transverse surfaces 67 that receive cam member 18 so as to prevent awl tip 12 from moving axially toward handle 24 when attachment end 16 of awl tip 12 is received in recess 27.

As shown in FIGS. 4 and 5, surgical bone awl 10 further defines a locking mechanism that locks awl tip 12 to shaft 20 when awl tip 12 is selectively connected to receiving end 21 of shaft 20. As shown in FIG. 6, the locking mechanism includes a clip member 30 attached to shaft 20 and defining a hook 31. Clip member 30 is formed of resilient material and is attached to shaft 20 by a pair of screws 32. Alternatively, it may be preferable to attach clip member 30 to shaft 20 by being welded or pinned. As shown in FIG. 6, a groove 33 that is elongated in the axial direction along shaft 20, is defined in shaft 20 in a configuration that receives clip member 30 therein. Moreover, groove 33 is deep enough to receive clip member 30 therein without protruding above the surrounding surface of shaft 20.

As shown in FIG. 6, an aperture 34 is defined through one end of groove 33 and disposed so as to permit hook 31 of clip member to protrude into recess 27 of shaft 20. As shown in FIGS. 4 and 5, clip member 30 resiliently biases hook 31 so as to engage lip 17 in a manner that locks awl tip 12 within recess 27 of shaft 20 when the attachment end 16 of awl tip 12 is received in recess 27 of shaft 20. Hook 31 is configured to engage lip 17 so as to prevent awl tip 12 from moving axially away from handle 24 when attachment end 16 of awl tip 12 is received in recess 27. Accordingly, hook 31, lip 17, slot 28 and cam member 18 cooperate so as to retain awl tip 12 fixed against axial movement with respect to shaft 20 while undergoing axially directed loads.

Surgical bone awl 10 further includes a release mechanism attached to the shaft 20. The release mechanism is configured to unlock the awl tip 12 that is selectively connected to attachment end 21 of shaft 20. The release mechanism enables awl tip 12 received in recess 27 of shaft 20, to be selectively disconnected from shaft 20 by being selectively withdrawn from recess 27. As shown in FIGS.

46, the release mechanism can include a hole 29 that is defined transversely through receiving end 21 of shaft 20 in communication with recess 27 from opposed surfaces of shaft 20.

The release mechanism can further include a button 36 that is movable within hole 29, which has a reduced diameter section 35 shown in FIG. 5. A reduced diameter portion 37 of button 36 is configured to pass through reduced diameter section 35 of hole 29, but the main body 42 of button 36 is too large to pass through reduced diameter section 35 of hole 29. Button 36 is retained in hole 29 by clip member 30 and reduced diameter section 35 of hole 29. As shown in FIG. 5, the axial length of main body 42 is sized so that when one end of main body 42 engages reduced diameter section 35 of hole 29, the opposite end of main body 42 presses against the inner surface 38 of clip member 30 and slightly deflects clip member 30 so that a portion of inner surface 38 is displaced away from contact with the bottom surface of groove 33 (FIG. 6). Alternatively, the axial length of main body 42 can be sized smaller than hole 29 so that a separate spring (not shown) can be used to bias button 36 within hole 29 of shaft 20 so that main body 42 of button 36 rests against the inner surface 38 of clip member 30.

Referring to FIG. 5, when the user pushes against reduced diameter portion 37 of button 36, main body 42 of button 36 moves in a direction transversely with respect to the axial direction of shaft 20. This transverse movement of button 36 moves button 36 in a first direction toward clip member 30. As main body 42 of button 36 presses against inner surface 38 of clip member 30, clip member 30 resiliently bends. At a predetermined degree of deflection, further bending of clip member 30 disengages hook 31 from lip 17 of awl tip 12 and thereby releases awl tip 12 from recess 27 of shaft 20.

Figure 2:
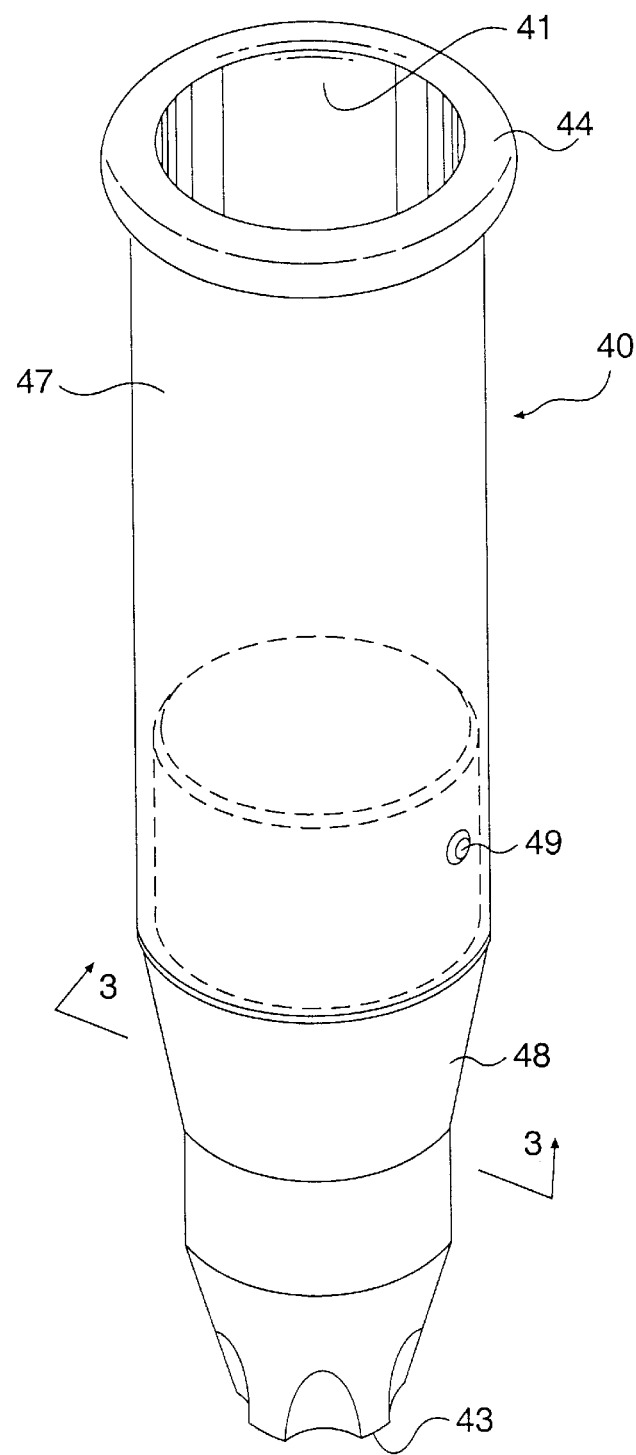
FIG. 2 is an elevated perspective view of a presently preferred embodiment of the retention sleeve component of the invention.
Figures 8, 9:
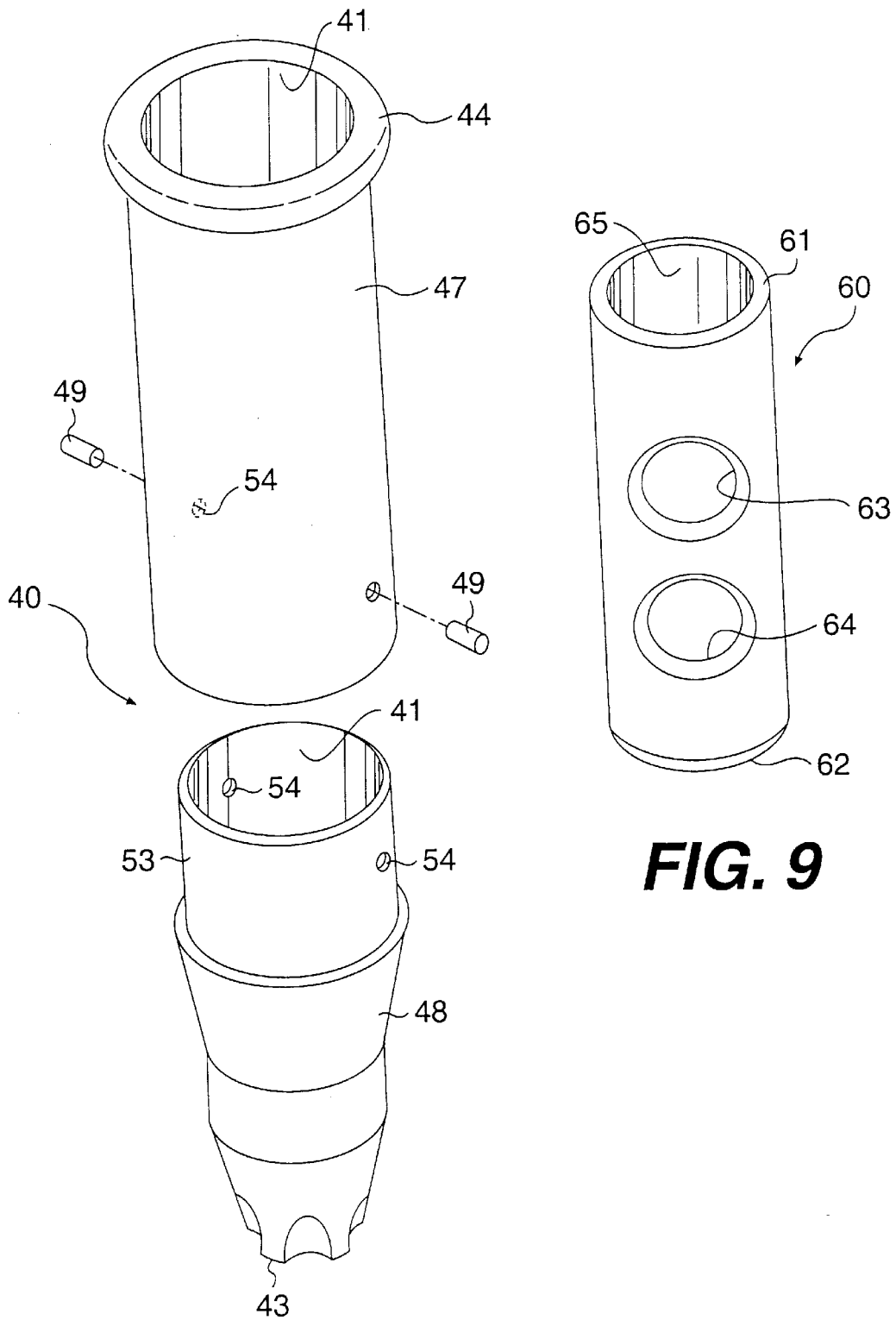
FIG. 8 is an elevated, perspective, assembly view of a presently preferred embodiment of the retention sleeve of the invention with the dashed lines indicating a hole that would otherwise be hidden in the view shown.
FIG. 9 is an elevated perspective view of a presently preferred embodiment of the protective sleeve of the invention.

In further accordance with the present invention, the surgical bone awl can include a hole-retention sleeve. As shown in FIGS. 1–3, 7A, and 8, a hole-retention sleeve is generally designated by the numeral 40 and defines a generally cylindrical shape. As shown in FIGS. 2 and 8, hole-retention sleeve 40 defines an axial passage 41 which surrounds at least a portion of awl tip 12. As shown in FIG. 1, axial passage 41 is also configured to surround at least part of receiving end 21 of shaft 20 so as to shield the activating mechanism, i.e., button 36, of the release mechanism from being accidentally moved in a manner that would result in release of awl tip 12 during use of awl 10 by the surgeon.

Figure 3:
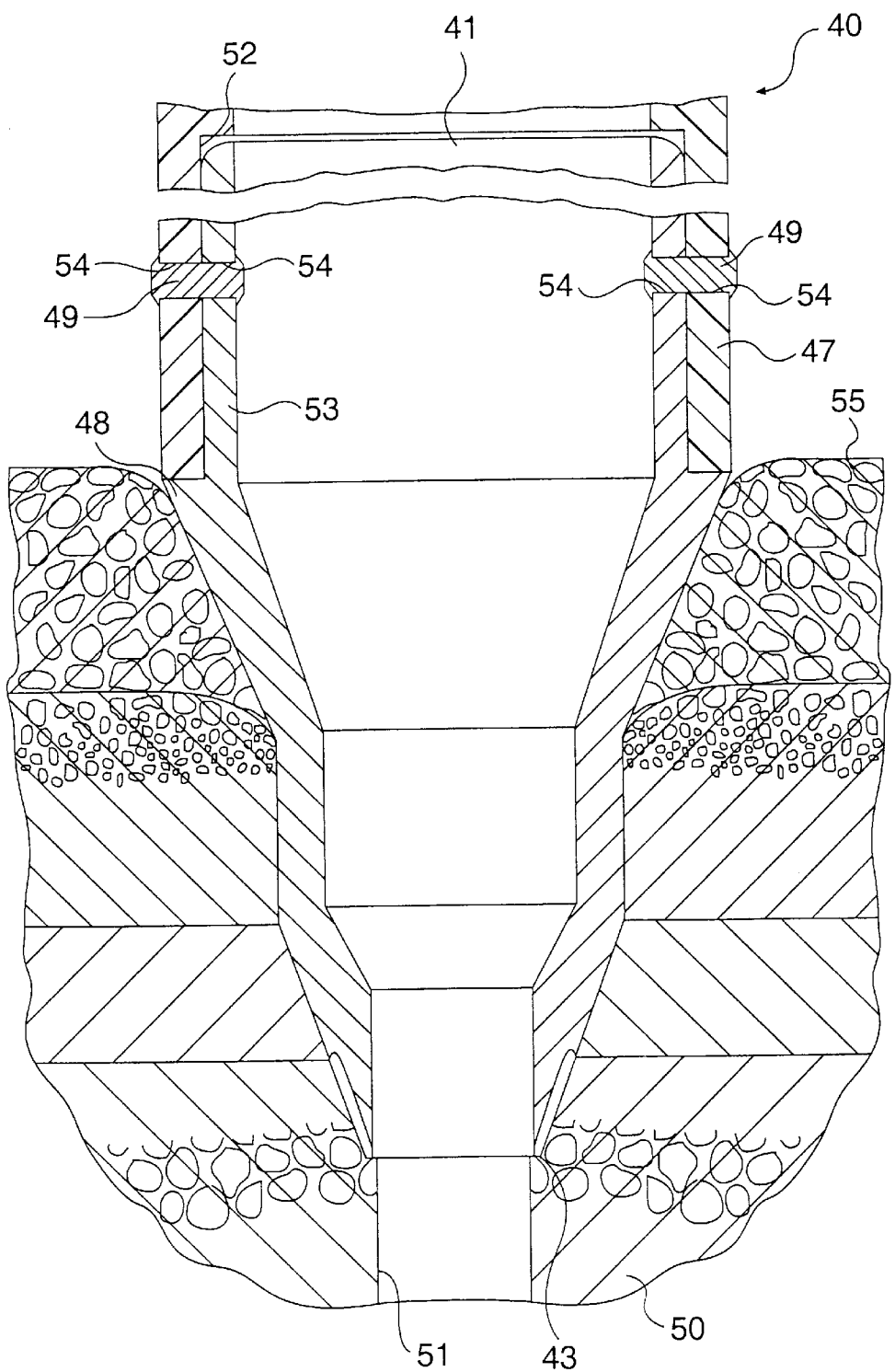
FIG. 3 is a cross-sectional view taken along a line of sight that looks in the direction of the arrows designated 3—3 in FIG. 2.

As shown in FIGS. 2 and 3, retention sleeve 40 further defines a forward cutting edge 43 that forms the annular cutting surface of one free edge of sleeve 40. As shown in FIGS. 1, 2 and 8, retention sleeve 40 defines a pressure collar 44 disposed around the free end thereof that is disposed opposite forward cutting edge 43. Pressure collar 44 enables the surgeon to leverage the application of pressure to cutting edge 43. In this way, the pressure applied by the surgeon to pressure collar 44 of sleeve 40 becomes concentrated at the location in the bone 50 (FIG. 3) that is in contact with forward cutting edge 43 of retention sleeve 40.

As shown in FIGS. 2, 3 and 8, retention sleeve 40 can be configured as two separate pieces that are integrated to form sleeve 40. One piece is the proximal element 47, and the other piece is the distal element 48. As shown in FIGS. 3 and 8, pressure collar 44 is formed at the free end of proximal element 47, and forward cutting edge 43 is formed at the free end of distal element 48.

As shown in FIG. 3, the other end of proximal element 47 defines a recess 52 that extends both circumferentially and for a predetermined axial distance from the free end of proximal element 47 opposite collar 44. The other end of distal element 48 defines a tongue portion 53 that is configured to be received in recess 52 of proximal element 47. Alternatively, the recess can be formed in distal element 48, and the tongue portion can be formed on proximal element 47. As shown in FIG. 8, mating holes 54 are configured to extend radially through the portion of proximal element 47 where recess 52 is formed and the end of distal element 48 where tongue portion 53 is formed. As shown in FIGS. 2 and 3, stainless steel fasteners such as bolts or rivets 49 are inserted through aligned mating holes 54 and secured therein to retain tongue portion 53 of distal element 48 within recess 52 of proximal element 47.

Proximal element 47 desirably can be formed of plastic material such as polytetrafluoroethylene. Fluorinated ethylene propylene also would work, but currently is more expensive. Distal element 48 desirably can be formed of material such as stainless steel that can hold a sharp edge for the formation of forward cutting edge 43.

As shown in FIG. 3, axial passage 41 is configured to allow the insertion of other surgical instruments besides awl tip 12, through passage 41 and thereby gain access to the bone site 51. As shown in FIG. 3, retention sleeve 40 is configured to remain in contact with the bone site 51 and to retain this location for access by the surgeon once the surgical bone awl 10 is withdrawn from within axial passage 41 of retention sleeve 40.

The awl of the present invention also can be used without hole-retention sleeve 40. When used without retention sleeve 40, a protective sleeve may be used in place of the retention sleeve. The protective sleeve may act to protect soft-tissue from being caught on features (such as a spring or button) that may be present on the tip or shaft of the awl. The protective sleeve also may be used to protect the manual awl tip release mechanism from being accidentally activated to release the awl tip during surgery or other times when release of the awl tip is not desired.

As embodied herein and indicated generally by the numeral 60 in FIGS. 7B, 7C and 9 for example, a protective sleeve 60 can be provided. Protective sleeve 60 is formed in the shape of an elongated hollow tubular member that has a first end 61 and an opposed second end 62. Like proximal element 47 of retention sleeve 40, protective sleeve 60 desirably can be formed of plastic material such as polytetrafluoroethylene. Fluorinated ethylene propylene also would work, but currently is more expensive. Like retention sleeve 40, protective sleeve 60 also can be configured so that it can be positioned around part or all of awl shaft 20 and tip 12. As shown in FIGS. 7B and 7C, sleeve 60 is configured to slide over the portion of shaft 20 in the vicinity of release button 36. As shown in FIG. 9, first end 61 and second end 62 are beveled for smooth sliding through tissue 55.

Sleeve 60 is provided with a pair of access holes 63, 64 that are sized to permit access to button 36. Access hole 63 is disposed the same distance from first end 61 of sleeve 60 as access hole 64 is disposed from second end 62 of sleeve 60. Because of this symmetric arrangement, sleeve 60 is configured so that either end 61 or end 62 can be slid onto shaft first, and one of access holes 63, 64 is certain to be axially positioned to provide access to button 36 upon being rotated into circumferential alignment with button 36 (as shown in FIG. 7B).

Moreover, the inner surface 65 of sleeve 60 is sized and configured for a snug fit around shaft 20 so that sleeve 60 can be manually rotated with respect to shaft 20, but will remain in position unless the user rotates sleeve 60 relative to shaft 20. In this way, sleeve 60 is configured so that the user can selectively rotate sleeve 60 around shaft 20 between the release mechanism access position shown in FIG. 7B and the release mechanism protection position shown in FIG. 7C and stay in the selected position, until the user rotates sleeve 60 from the selected position.

In an alternative embodiment (not shown) of protective sleeve 60, the length of sleeve 60 can be just long enough to shield button 36. This alternative embodiment does not need any access holes, and can be selectively moved axially so as to either cover button 36 or not, according to the axial position of the protective sleeve along shaft 20.

In operation, attachment end 16 of an awl tip 12 would be inserted into shaft recess 27 in receiving end 21 of awl shaft 20. As shown in FIG. 5 for example, hook 31 of clip member 30 has an inclined surface 39, and lip 17 of attachment end 16 of awl tip 12 has a complementary inclined surface 19. As shown in FIG. 4, hook 31 of clip member 30 is biased toward axis 26 of shaft 30, but is formed of resilient material that moves radially outwardly away from the central axis 26 of shaft 30 as attachment end 16 of awl tip 12 is inserted axially into recess 27. Accordingly, the camferred surface 19 of lip 17 bypasses the inclined forward surface 39 of hook 31.

As shown in FIG. 5, when attachment end 16 of awl tip 12 is inserted deep enough into recess 27 of shaft 20 so that forward surface 46 of lip 17 nears bottom 45 of recess 27, cam member 18 butts against the transverse surfaces 67 of slot 28 and hook 31 of clip member 30 becomes engaged beneath underside surface 15 of lip 17. The transverse surfaces 67 of slot 28 prevent cam member 18 of awl tip 12 from moving any further toward handle 24 of awl 10. Thus, awl tip 12 is secured against axial movement relative to shaft 20 of awl 10. In addition, cam member 18 is configured with a shape that is nonrotatably received between the opposed axial surfaces 66 of slot 28 formed in receiving end 21 of shaft 20. Thus, awl tip 12 is secured against rotational movement relative to shaft 20 of awl 10. Accordingly, cam member 18 and slot 28 are configured to cooperate to control both the axial position and the rotational position, of awl tip 12 relative to awl shaft 20.

During the use of bone awl 10, retention sleeve 40 surrounds the awl tip receiving end 21 of awl 10 as the surgeon uses bone awl 10 to contact the bone surface with the working surface 14 of awl tip 12. When the surgeon feels cutting edge 43 of retention sleeve 40 seating against the bone 50 after the entry hole 51 is made with working end 14 of awl tip 12, the surgeon applies pressure to collar 44 of retention sleeve 40 while also applying a twisting (rotational) motion about axis 26 so as to push cutting edge 43 of retention sleeve 40 against and into the bone surface to cut through the bone surface as shown in FIG. 3 for example. Cutting edge 43 becomes anchored in the bone 50 even after awl tip 12 is withdrawn therefrom as shown in FIG. 3 for example. Additional surgical instruments can be passed through passage 41 of retention sleeve 40 to address the same site on the bone that has been addressed and penetrated by awl 10 and cutting edge 43 of retention sleeve 40. Moreover, retention sleeve 40 retains the surgeon's access to the penetrated bone site, thus eliminating the need for the surgeon to relocate the site once tissue 55 has closed over it upon withdrawal of the awl 10.

When it is desired to replace a particular awl tip, the operator presses button 36 in a direction transversely relative to central axis 26 of shaft 30 so as to move clip member 30 away from central axis 26. Accordingly, hook 31 is moved away from engagement with underside 15 of lip 17. This permits lip 17 to slide past hook 31 as awl tip 12 is withdraw from within recess 27 of shaft 20.

It can be seen that the present invention provides a novel surgical awl 10 with exchangeable tips 12, a retention and protection sleeve 40, and an alternative protective sleeve 60. While preferred embodiments of the invention have been shown and described, modifications and variations may be made thereto by those of ordinary skill in the art without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A surgical bone awl apparatus, comprising:

a shaft having a receiving end and a gripping end disposed generally opposite said receiving end;

a handle attached to said gripping end of said shaft and configured to facilitate awl manipulation;

an awl tip defining a working end and an attachment end disposed opposite said working end;

said receiving end of said shaft being configured to be selectively connected to said attachment end of said awl tip;

a locking mechanism attached to said shaft and configured to lock said awl tip selectively connected to said receiving end of said shaft so as to enable said awl tip to remain fixed with respect to said shaft while undergoing torsional, bending, and axial loads in all directions;

a release mechanism attached to said shaft and configured to unlock said awl tip selectively connected to said receiving end of the shaft so as to enable said awl tip to be selectively disconnected from said receiving end of said shaft;

a hole-retention sleeve defining a cylindrical shape and an axial passage which surrounds at least part of said awl tip and at least part of said receiving end of said shaft;

said retention sleeve defining a forward cutting edge; and said retention sleeve defining a pressure collar disposed opposite said forward cutting edge.

2. An apparatus as in claim 1, wherein said axial passage is configured to allow passage of a surgical instrument therethrough.

3. An apparatus as in claim 1, wherein said axial passage is configured to surround at least part of said receiving end of said shaft so as to shield said release mechanism from being accidently activated to release said awl tip.

4. A surgical bone awl apparatus, comprising:

a shaft having a receiving end and a gripping end disposed generally opposite said receiving end;

a handle attached to said gripping end of said shaft and configured to facilitate awl manipulation;

an awl tip defining a working end and an attachment end disposed opposite said working end;

said receiving end of said shaft being configured to be selectively connected to said attachment end of said awl tip;

a locking mechanism attached to said shaft and configured to lock said awl tip selectively connected to said receiving end of said shaft so as to enable said awl tip to remain fixed with respect to said shaft while undergoing torsional, bending, and axial loads in all directions;

a release mechanism attached to said shaft and configured to unlock said awl tip selectively connected to said receiving end of the shaft so as to enable said awl tip to be selectively disconnected from said receiving end of said shaft;

a protective sleeve defining a cylindrical shape and an axial passage which surrounds at least part of said receiving end of said shaft so as to shield said release mechanism from being accidently activated to release said awl tip.

5. An apparatus as in claim 1, wherein:

said receiving end of said shaft defines a recess therein;

said attachment end of said awl tip defines a radially extending lip received in said recess; and said locking mechanism includes a clip member connected to said shaft and defining a hook configured to engage said lip so as to prevent axial movement of said awl tip away from said handle when said attachment end of said awl tip is received in said recess.

6. An apparatus as in claim 5, wherein said clip member resiliently biases said hook to engage said lip when said attachment end of said awl tip is received in said recess.

7. An apparatus as in claim 5, wherein said release mechanism includes a button moveably disposed in said shaft and configured to disengage said hook from said lip and thereby release said awl tip from said recess when said button is moved in a first direction.

8. An apparatus as in claim 7, wherein:

said attachment end of said awl tip defines a cam member; and said locking mechanism includes a slot configured to receive said cam member so as to prevent rotation of said awl tip relative to said shaft when said attachment end of said awl tip is received in said recess.

9. An apparatus as in claim 7, wherein:

said attachment end of said awl tip defines a cam member; and said locking mechanism includes a slot configured to receive said cam member so as to prevent axial movement of said awl tip toward said handle when said attachment end of said awl tip is received in said recess.

10. A surgical bone awl apparatus, comprising:

an awl tip defining a working end and an opposite attachment end, said attachment end defining a cam member, said attachment end defining a radially extending lip;

a shaft having a receiving end and a gripping end disposed generally opposite said receiving end, said receiving end defining a recess therein, said recess being configured to receive said attachment end of said awl tip therein;

a handle attached to said gripping end of said shaft and configured to facilitate awl manipulation;

a locking mechanism including a clip member attached to said shaft and defining a hook, said clip member resiliently biasing said hook to engage said lip to lock said awl tip received in said recess so as to enable said awl tip to remain fixed against axial movement with respect to said shaft while undergoing axially directed loads;

said locking mechanism includes a slot configured to receive said cam so as to prevent rotation of said awl tip relative to said shaft when said attachment end of said awl tip is received in said recess;

a button moveably disposed in said shaft and configured to disengage said hook from said lip and thereby release said awl tip from said recess when said button is moved in a first direction;

a hole-retention sleeve defining a cylindrical shape and an axial passage which surrounds said awl tip, said axial passage being configured to surround at least part of said attachment end of said shaft so as to shield said button from being accidentally moved so as to release said awl tip;

said retention sleeve defining a forward cutting edge and a pressure collar disposed opposite said forward cutting edge; and said axial passage being configured to allow passage of a surgical instrument therethrough.

* * * * *